US008236750B2

(12) United States Patent
Schaefer et al.

(10) Patent No.: US 8,236,750 B2
(45) Date of Patent: Aug. 7, 2012

(54) COMPOSITION COMPRISING A PULMONARY SURFACTANT AND A TNF-DERIVED PEPTIDE

(75) Inventors: Klaus P. Schaefer, Constance (DE); Stefan-Lutz Wollin, Meersburg (DE); Ingeborg Muehldorfer, Constance (DE)

(73) Assignee: Nycomed GmbH, Constance (DE)

( * ) Notice: Subject to any disclaimer, the term of this patent is extended or adjusted under 35 U.S.C. 154(b) by 605 days.

(21) Appl. No.: 11/658,727

(22) PCT Filed: Jul. 27, 2005

(86) PCT No.: PCT/EP2005/053672

§ 371 (c)(1), (2), (4) Date: Jan. 29, 2007

(87) PCT Pub. No.: WO2006/013183

PCT Pub. Date: Feb. 9, 2006

(65) Prior Publication Data

US 2007/0299003 A1 Dec. 27, 2007

(30) Foreign Application Priority Data

Aug. 6, 2004 (EP) .................................... 04103808

(51) Int. Cl.
*A61K 38/10* (2006.01)

(52) U.S. Cl. ........................................ 514/1.1; 424/85.1

(58) Field of Classification Search ........................ None
See application file for complete search history.

(56) References Cited

U.S. PATENT DOCUMENTS

| | | | | |
|---|---|---|---|---|
| 4,828,844 | A | 5/1989 | Röntgen-Odenthal et al. | |
| 4,944,941 | A * | 7/1990 | Ammann ..................... | 424/85.5 |
| 5,874,406 | A | 2/1999 | Schafer et al. | |
| 6,315,983 | B1 | 11/2001 | Eistetter | |
| 6,982,075 | B2 | 1/2006 | Taut | |
| 2003/0091509 | A1 | 5/2003 | Häfner et al. | |
| 2003/0185791 | A1 | 10/2003 | Lucas et al. | |

FOREIGN PATENT DOCUMENTS

| | | | |
|---|---|---|---|
| DE | 32 29 179 | A1 | 2/1984 |
| DE | 198 51 617 | A1 | 5/2000 |
| EP | 0 100 910 | B1 | 2/1984 |
| EP | 0 110 498 | B1 | 6/1984 |
| EP | 0 119 056 | B1 | 9/1984 |
| EP | 0 145 005 | B1 | 6/1985 |
| EP | 0 251 449 | B1 | 1/1988 |
| EP | 0 348 967 | A2 | 1/1990 |
| EP | 0 368 823 | B2 | 5/1990 |
| EP | 0 593 094 | B1 | 4/1994 |
| EP | 0 286 011 | B1 | 10/1994 |
| EP | 0 977 577 | B1 | 2/2000 |
| EP | 1 131 055 | B1 | 9/2001 |
| WO | 86/03408 | A1 | 6/1986 |
| WO | 87/06943 | A1 | 11/1987 |
| WO | 88/03170 | A1 | 5/1988 |
| WO | 89/04326 | A1 | 5/1989 |
| WO | 91/18015 | A1 | 11/1991 |
| WO | 92/22315 | A1 | 12/1992 |
| WO | 95/32992 | A1 | 12/1995 |
| WO | 97/26863 | A1 | 7/1997 |
| WO | 97/35882 | A1 | 10/1997 |
| WO | 00/09149 | A1 | 2/2000 |
| WO | 01/76619 | A1 | 10/2001 |
| WO | 02/100871 | A1 | 12/2002 |
| WO | 03/033014 | A2 | 4/2003 |

OTHER PUBLICATIONS

Ngo et al., 1994, The Protein Folding Problem and Tertiary Structure Prediction, Merz and Le Grnad, eds., Birkhauser, Boston, pp. 491-495.*

Wells, 1990, Biochemistry 29:8509-8517.*

Bernard, G. R., et al., "Report of the American-European consensus conference on ARDS: definitions, mechanisms, relevant outcomes and clinical trial coordination", *Intensive Care Med*, vol. 20, pp. 225-232, (1994).

Lucas, R., et al., "Mapping the Lectin-Like Activity of Tumor Necrosis Factor", *Science*, vol. 263, pp. 814-817, (1994).

Frerking, I., et al., "Pulmonary surfactant: functions, abnormalities and therapeutic options", *Intensive Care Med*, vol. 27, pp. 1699-1717, (2001).

Mikawa, et al., "Intratracheal Application of Recombinant Surfactant Protein-C Surfactant to Rabbits Attenuates Acute Lung Injury Induced by Intratracheal Acidified Infant Formula", Anesth Analg, vol. 98, pp. 1273-1279, (2004).

* cited by examiner

*Primary Examiner* — Prema Mertz

(74) *Attorney, Agent, or Firm* — Nath, Goldberg & Meyer; Sheldon M. McGee

(57) ABSTRACT

The invention relates to the combination of a pulmonary surfactant and a TNF-derived peptide and its use for the treatment of respiratory disease.

19 Claims, 1 Drawing Sheet

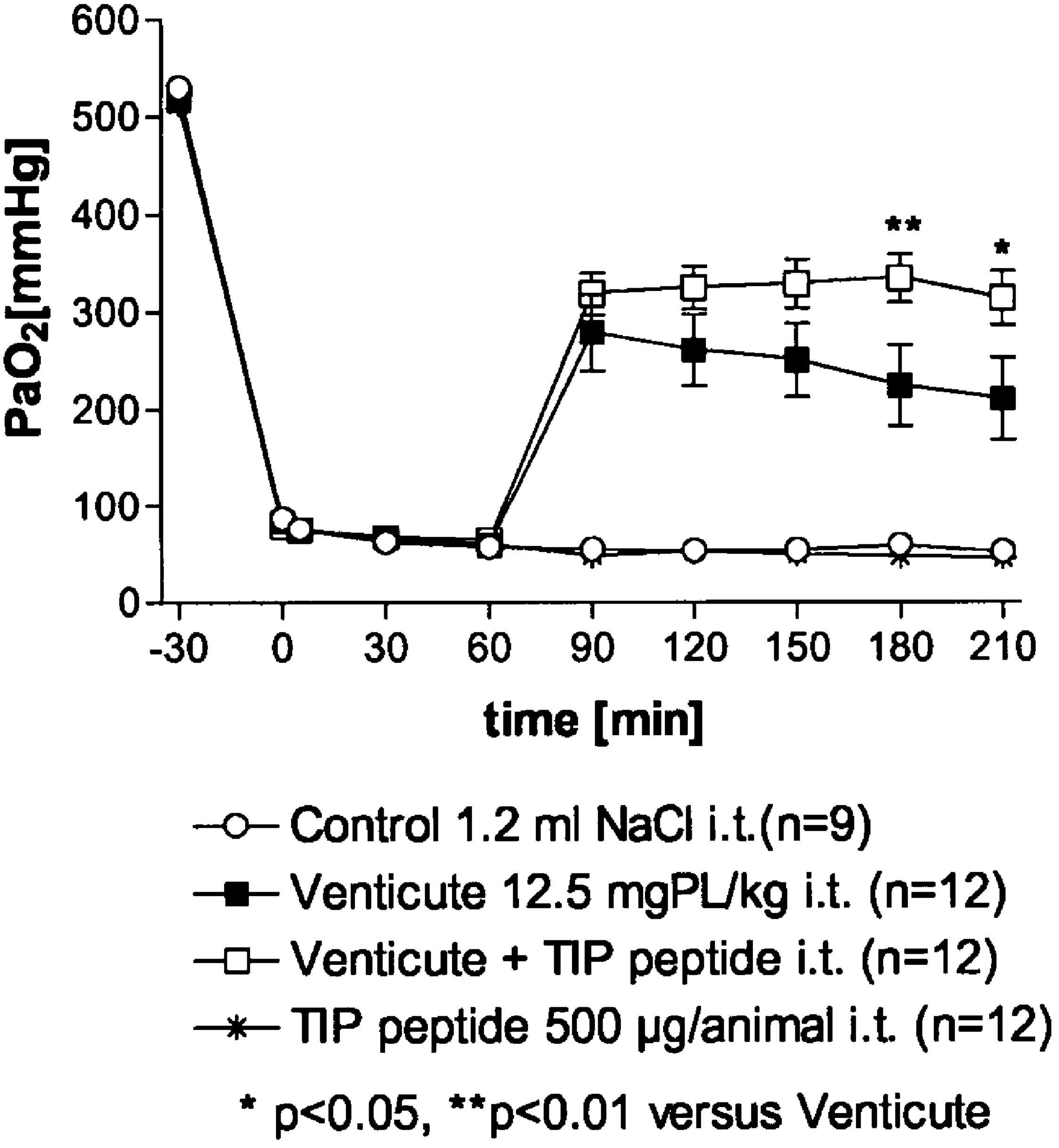
600
500
400
300
200
100
0
$PaO_2$[mmHg]
**
*
-30
0
30
60
90
120
150
180
210
time [min]
Control 1.2 ml NaCl i.t.(n=9)
Venticute 12.5 mgPL/kg i.t. (n=12)
Venticute + TIP peptide i.t. (n=12)
TIP peptide 500 μg/animal i.t. (n=12)
* p<0.05, **p<0.01 versus Venticute

COMPOSITION COMPRISING A PULMONARY SURFACTANT AND A TNF-DERIVED PEPTIDE

FIELD OF APPLICATION OF THE INVENTION

The invention relates to the combination of certain known active compounds for therapeutic purposes. The compounds used in the combination according to this invention are known pulmonary surfactants and a known active compound derived from TNF. Their combined use in the sense according to this invention for therapeutic purposes has not yet been described in prior art.

PRIOR ART

ARDS (Adult Respiratory Distress Syndrome) is a descriptive expression which is applied to a large number of acute, diffuse infiltrative pulmonary lesions of differing etiology if they are associated with a severe gas exchange disorder (in particular arterial hypoxemia) [G. R. Bernard et al.: Report of the American-European consensus conference on ARDS: definitions, mechanisms, relevant outcomes and clinical trial coordination; Intensive Care Medicine, 1994, 20:225-232]. The expression ARDS is also used for IRDS (Infant Respiratory Distress Syndrome) because of the numerous common clinical and pathological features. If, in the case of IRDS, the lung surfactant deficiency caused by premature birth is predominant, then in the case of ARDS a lung surfactant malfunction is caused by the disease of the lung based on differing etiologies. Triggering causes for an ALI (Acute Lung Injury) including ARDS can, for example, be (cited in accordance with Harrison's Principles of Internal Medicine 10th Ed. 1983 McGraw-Hill Int. Book Comp.) diffuse pulmonary infections (e.g. due to viruses, bacteria, fungi), aspiration of, for example, gastric juice or in the case of near-drowning, inhalation of toxins or irritants (e.g. chlorine gas, nitrogen oxides, smoke), direct or indirect trauma (e.g. multiple fractures or pulmonary contusion), systemic reactions to inflammations outside the lung (e.g. hemorrhagic pancreatitis, gram-negative septicemia), transfusions of high blood volumes or alternatively after cardiopulmonary bypass. In patients suffering from ARDS, lung surfactant function is impaired so that the alveolar surfactant layer does not prevent lung atelectasis and does not maintain physiologic lung functions required for oxygenation.

In the healthy lung, pulmonary endothelium regulates the exchange of fluid, solutes, macromolecules, and cells between vascular and tissue spaces. With inflammation abound in ARDS, the endothelial barrier becomes more permissive for exchange leading to interstitial and alveolar edema formation. This process leads to a further impairment of oxygenation.

Presently, the therapy of ARDS mainly consists in the earliest possible application of different forms of ventilation (e.g. raising of the oxygen concentration of the respiratory air) up to extracorporeal membrane oxygenation. The specific use of various ventilation techniques has only led to a small lowering of mortality and including the risk of damaging the lungs by ventilation with pressure and high $FiO_2$ (Fraction of Inspired Oxygen; proportion of oxygen in the respiratory air). In particular, ARDS patients whose lungs have been damaged by ventilation need even higher pressures and higher $FiO_2$ to obtain an adequate oxygenation of the blood.

Because surfactant function is impaired in ARDS, surfactant replacement therapy is thought to improve lung function and oxygenation in ARDS. It has also proven suitable to treat IRDS by introducing pulmonary surfactant preparations into the lungs of the children concerned. WO01076619 and WO003033014 describe the use of pulmonary surfactant preparations for the prophylaxis, early treatment or treatment of acute pulmonary diseases such as ARDS, IRDS or ALI.

Lucas et al. [Lucas R et al. (1994) Science 263: 814] firstly disclosed a new TN F-derived peptide having the amino add sequence CGQRETPEGAEAKPWYC. This peptide has also been subject in the international patent application WO0009149, which describes the use of TNF-derived peptides in the treatment of edema, in particular lung edema.

SUMMARY OF THE INVENTION

It is the object of the present invention to make available a pharmaceutical composition suited for the treatment of ARDS, IRDS, ALI or lung edema.

Surprisingly, it has now been found that the combined use of a pulmonary surfactant and a TNF-derived peptide is beneficial in the treatment of ARDS, IRDS, ALI or lung edema.

Thus, the invention relates to pharmaceutical compositions comprising a pulmonary surfactant and a peptide characterized by an amino acid sequence comprising the hexamer $TX_1EX_2X_3E$, wherein $X_1$, $X_2$ and $X_3$ can be any natural or unnatural amino acid, its use as a medicament and methods for treating ARDS, IRDS, ALI or lung edema.

Accordingly, the invention relates in a first aspect to a pharmaceutical composition comprising an effective amount of a pulmonary surfactant and an effective amount of a peptide characterized by an amino acid sequence comprising the hexamer $TX_1EX_2X_3E$, wherein $X_1$, $X_2$ and $X_3$ can be any natural or unnatural amino acid.

In another aspect of present invention there is provided a pharmaceutical composition comprising an effective amount of a pulmonary surfactant and an effective amount of a peptide characterized by an amino acid sequence comprising the hexamer TPEGAE (SEQ ID NO:1).

In further aspects of present invention the peptide of the pharmaceutical composition is further characterized by a chain of 7 to 17 or 11-16 or 13-15 contiguous amino acids or a chain of 14 amino acids derived from the region of human TNF-$\alpha$ from Ser100 to Glu116

In another aspect of present invention there is provided a pharmaceutical composition comprising an effective amount of a pulmonary surfactant and an effective amount of a peptide characterized by an amino acid sequence comprising QRETPEGAEAKPWY (SEQ ID NO:2).

In another aspect of present invention there is provided a pharmaceutical composition comprising an effective amount of a pulmonary surfactant and an effective amount of a peptide characterized by an amino acid sequence comprising CGQRETPEGAEAKPWYC (SEQ ID NO:3).

In another aspect of present invention there is provided a pharmaceutical composition comprising an effective amount of a pulmonary surfactant and an effective amount of one of the herein before mentioned peptides, wherein the peptide is synthetic.

In another aspect of present invention there is provided a pharmaceutical composition comprising an effective amount of a pulmonary surfactant and an effective amount of one of the herein before mentioned peptides, wherein the peptide is circularized.

In another aspect of present invention there is provided a pharmaceutical composition comprising an effective amount of a pulmonary surfactant and an effective amount of one of the herein before mentioned peptides, wherein the pulmonary surfactant is selected from the group consisting of PORAC- TANT ALFA, BERACTANT, BOVACTANT, COLFOSCERIL PALMITATE, SURFACTANT-TA, CALFACTANT, PUMACTANT, LUSUPULTIDE and SINAPULTIDE.

In another aspect of present invention there is provided a pharmaceutical composition comprising an effective amount of a pulmonary surfactant and an effective amount of one of the herein before mentioned peptides for use as a medicament.

In another aspect of present invention there is provided a fixed combination of (1) an effective amount of a pulmonary surfactant and (2) an effective amount of one of the herein before mentioned peptides, and (3) optionally a pharmaceutically acceptable carrier.

In another aspect of present invention there is provided a pharmaceutical composition in powder form comprising as a fixed combination of (1) an effective amount of a pulmonary surfactant and (2) an effective amount of one of the herein before mentioned peptides, and (3) optionally a pharmaceutically acceptable carrier.

In another aspect of present invention there is provided a pharmaceutical composition in liquid form comprising as a fixed combination of (1) an effective amount of a pulmonary surfactant and (2) an effective amount of one of the herein before mentioned peptides, and (3) optionally a pharmaceutically acceptable carrier.

In another aspect of present invention there is provided a pharmaceutical composition for intratracheally or intrabronchially instillation comprising as a fixed combination (1) an effective amount of a pulmonary surfactant and (2) an effective amount of one of the herein before mentioned peptides, and (3) optionally a pharmaceutically acceptable carrier.

In another aspect of present invention there is provided a pharmaceutical composition for inhalation comprising as a fixed combination (1) an effective amount of a pulmonary surfactant and (2) an effective amount of one of the herein before mentioned peptides, and (3) optionally a pharmaceutically acceptable carrier.

In another aspect of present invention there is provided a free combination of (1) an effective amount of a pulmonary surfactant and optionally a pharmaceutically acceptable carrier and (2) an effective amount of one of the herein before mentioned peptides and optionally a pharmaceutically acceptable carrier.

In another aspect of present invention there is provided a pharmaceutical composition in liquid form comprising as a free combination (1) an effective amount of a pulmonary surfactant and optionally a pharmaceutically acceptable carrier and (2) an effective amount of one of the herein before mentioned peptides and optionally a pharmaceutically acceptable carrier.

In another aspect of present invention there is provided a pharmaceutical composition in powder form comprising as a free combination (1) an effective amount of a pulmonary surfactant and optionally a pharmaceutically acceptable carrier and (2) an effective amount of one of the herein before mentioned peptides and optionally a pharmaceutically acceptable carrier.

In another aspect of present invention there is provided a pharmaceutical composition for intratracheally or intrabronchially instillation comprising as a free combination (1) an effective amount of a pulmonary surfactant and optionally a pharmaceutically acceptable carrier and (2) an effective amount of one of the herein before mentioned peptides and optionally a pharmaceutically acceptable carrier.

In another aspect of present invention there is provided a pharmaceutical composition for inhalation comprising as a free combination (1) an effective amount of a pulmonary surfactant and optionally a pharmaceutically acceptable carrier and (2) an effective amount of one of the herein before mentioned peptides and optionally a pharmaceutically acceptable carrier.

In another aspect of present invention there is provided a pharmaceutical composition comprising an effective amount of a pulmonary surfactant and an effective amount of one of the herein before mentioned peptides for use as a medicament.

In another aspect of present invention there is provided the use of a pharmaceutical composition comprising an effective amount of a pulmonary surfactant and an effective amount of one of the herein before mentioned peptides for the manufacture of a medicament for the treatment of a disease selected from the group consisting of ALI, IRDS, ARDS and lung edema.

In another aspect of present invention there is provided the use of a pharmaceutical composition comprising an effective amount of a pulmonary surfactant and an effective amount of one of the herein before mentioned peptides for the treatment of a disease selected from the group consisting of ARDS, IRDS, ALI and lung edema.

In another aspect of present invention there is provided a method for treating ARDS, IRDS, ALI or lung edema by administering to a patient in need thereof an effective amount of a pharmaceutical composition pharmaceutical composition comprising an effective amount of a pulmonary surfactant and an effective amount of one of the herein before mentioned peptides.

In another aspect of present invention there is provided a method for treating ARDS, IRDS, ALI or lung edema by simultaneously administering to a patient in need thereof an effective amount of a pharmaceutical composition pharmaceutical composition comprising an effective amount of (1) a pulmonary surfactant and (2) a circularized peptide comprising the amino adds CGQRETPEGAEAKPWYC (SEQ ID NO:3).

In another aspect of present invention there is provided a method for treating ARDS, IRDS, ALI or lung edema by administering in succession, close in time or remote in time, in any order whatever to a patient in need thereof an effective amount of a pharmaceutical composition pharmaceutical composition comprising an effective amount of (1) a pulmonary surfactant and (2) a circularized peptide comprising the amino acids CGQRETPEGAEAKPWYC (SEQ ID NO:3).

DETAILED DESCRIPTION OF THE INVENTION

Subject matter of present invention is a combination comprising a pulmonary surfactant and a TNF-derived peptide and the use of this combination in the treatment of ARDS, IRDS ALI or lung edema.

The invention thus relates to a pharmaceutical composition comprising an effective amount of a pulmonary surfactant and an effective amount of a peptide characterized by an amino acid sequence comprising the hexamer $TX_1EX_2X_3E$, wherein $X_1$, $X_2$ and $X_3$ can be any natural or unnatural amino acid, and the combined use of these single compounds to treat ARDS, IRDS, ALI or lung edema.

The "pulmonary surfactant" useful in this invention may be any compound or pulmonary surfactant preparation that is known to have the same surface-active properties as natural pulmonary surfactant; natural pulmonary surfactant reduces, for example, the surface tension in the alveoli.

A simple and rapid in vitro test with which the surface activity of pulmonary surfactant can be determined is, for example, the so-called Wilhelmy balance [Goerke, J. Biochim. Biophys. Acta, 344: 241-261 (1974), King R. J. and Clements J. A., Am. J. Physicol. 223: 715-726 (1972)]. This method gives information on the pulmonary surfactant quality, measured as the action of a pulmonary surfactant of achieving a surface tension of almost zero mN/m. Another measuring device for determining the surface activity of pulmonary surfactant is the pulsating bubble surfactometer [Possmayer F. et al., Prog. Resp. Res., Ed. v. Wichert, Vol. 18: 112-120 (1984)]. The activity of a pulmonary surfactant preparation can also be determined by means of in vivo tests, for example as described by Hafner et al. [D. Häfner et al.: Effects of rSP-C surfactant on oxygenation and histology in a rat lung lavage model of acute lung injury. Am. J. Respir. Crit. Care Med. 1998, 158: 270-278].

A group of known pulmonary surfactant preparations and their modifications that may be usefully as pulmonary surfactant employed in the present invention include pulmonary surfactant preparations having the function of natural pulmonary surfactant. Preferred pulmonary surfactant preparations are those which, for example, have activity in the tests described above. Particularly preferred pulmonary surfactant preparations are those which exhibit increased activity in such a test in comparison with natural, in particular human, pulmonary surfactant. In this context, these can be compositions which only contain phospholipids, but also compositions which, apart from the phospholipids, inter alia additionally contain pulmonary surfactant protein.

Preferred phospholipids according to the invention are dipalmitoylphosphatidylcholine (DPPC), palmitoyloleylphosphatidylglycerol (POPG) and/or phosphatidylglycerol (PG). Particularly preferably, the phospholipids are mixtures of various phospholipids, in particular mixtures of dipalmitoylphosphatidylcholine (DPPC) and palmitoyloleylphosphatidylglycerol (POPG), preferably in the ratio from 7 to 3 to 3 to 7.

Commercial products which may be mentioned as pulmonary surfactant preparations are

- CUROSURF® (INN: PORACTANT ALFA) (Serono, Pharma GmbH, Unterschleiβheim), a natural surfactant from homogenized porcine lungs;
- SURVANTA® (INN: BERACTANT) (Abbott GmbH, Wiesbaden), extract of bovine lungs;
- ALVEOFACT® (INN: BOVACTANT) (Boehringer Ingelheim), extract of bovine lungs;
- EXOSURF® (INN: COLFOSCERIL PALMITATE) (Glaxo SmithKline), a synthetic phospholipid containing excipients;
- SURFACTEN® (INN: SURFACTANT-TA) (Mitsubishi Pharma Corporation), a pulmonary surfactant extracted from bovine lungs;
- INFASURF® (INN: CALFACTANT) (Forest Pharmaceuticals), a surfactant extracted from calf lungs;
- ALEC® (INN: PUMACTANT) (Britannia Pharmaceuticals), an artificial surfactant of DPPC and PG; and
- BLES® (BLES Biochemical Inc.), a bovine lipid extract surfactant.

Suitable pulmonary surfactant proteins are both the proteins obtained from natural sources, such as pulmonary lavage or extraction from amniotic fluid, and the proteins prepared by genetic engineering or chemical synthesis. According to the invention, in particular the pulmonary surfactant proteins designated by SP-B (Surfactant Protein-B) and SP-C (Surfactant Protein-C) and their modified derivatives are of interest. The amino acid sequences of these pulmonary surfactant proteins, their isolation or preparation by genetic engineering are known (e.g. from WO 8603408, EP 0251449, WO 8904326, WO 8706943, WO 8803170, WO 9100871, EP 0368823 and EP 0348967). Modified derivatives of the pulmonary surfactant proteins designated by SP-C, which differ from human SP-C by the replacement of a few amino acids, are described, for example, in WO 9118015 and WO 9532992. Particularly to be emphasized in this connection are the recombinant SP-C (rSP-C) derivatives which are disclosed in WO 9532992, in particular those which differ from human SP-C in positions 4 and 5 by the substitution of cysteine by phenylalanine and in position 32 by the substitution of methionine by isoleucine [designated herein as rSP-C (FF/I) or LUSUPULTIDE (INN) or VENTICUTE®)]. Modified derivatives of pulmonary surfactant proteins are also understood as meaning those proteins which have a completely originally designed amino acid sequence with respect to their pulmonary surfactant properties, such as are described in EP 0593094 and WO 9222315. Preferably, the polypeptide KL4 (INN: SINAPULTIDE, SURFAXIN®) may be mentioned in this connection. The name pulmonary surfactant protein, according to the invention, also comprises mixtures of different pulmonary surfactant proteins. In EP 0100910, EP 0110498, EP 0119056, EP 0145005 and EP 0286011 phospholipid compositions with and without pulmonary surfactant proteins are described which are likewise suitable as components of the preparations.

As further constituents which can be present in pulmonary surfactant preparations, fatty acids such as palmitic acid may be mentioned. The pulmonary surfactant preparations can also contain electrolytes such as calcium, magnesium and/or sodium salts (for example calcium chloride, sodium chloride and/or sodium hydrogencarbonate) in order to establish an advantageous viscosity. Preferred pulmonary surfactant preparations according to the invention contain 80 to 95% by weight of phospholipids, 0.5 to 3.0% by weight of pulmonary surfactant proteins, 3 to 15% by weight of fatty acid, preferably palmitic add, and 0 to 3% by weight of calcium chloride.

The pulmonary surfactant preparations are prepared by processes known per se and familiar to the person skilled in the art, for example as described in WO 9532992. According to the invention, the pulmonary surfactant preparations are preferably lyophilized and in particular spray-dried pulmonary surfactant preparations. Lyophilized preparations are disclosed, for example, in WO 9735882, WO 9100871 and DE 3229179. WO 9726863 describes a process for the preparation of powdered pulmonary surfactant preparations by spray drying. According to the invention, preparations prepared in this way are preferred.

TNF-derived peptides which may be used in a pharmaceutical composition in accordance with present invention are peptides comprising a chain of 7 to 17, preferably a chain of 11 to 16, more preferably a chain of 13 to 15 and most preferably a chain of 14 or 16 contiguous amino acids derived from the region of human TNF-α from Ser100 to Glu116 or from the region of mouse TNF-α from Ser99 to Glu115. These peptides may be used in a combination with a pulmonary surfactant for the manufacture of a medicament for treating ARDS, IRDS, ALI or lung edema.

Specifically, peptides of present are those peptides characterized by an amino acid sequence comprising the hexamer $TX_1EX_2X_3E$, wherein $X_1$, $X_2$ and $X_3$ can X.sub.1, X.sub.2 and X.sub.3 can be any natural or unnatural amino acid. More specifically, TNF-derived peptides of present are those peptides, wherein the hexamer has the sequence TPEGAE (SEQ ID NO:1). Particularly preferred is a peptide comprising the amino acids QRETPEGAEAKPWY (SEQ ID NO:2) such as CGQRETPEGAEAKPWYC (SEQ ID NO:3). This peptide has been described by Lucas et al. [Lucas R et al. (1994) Science 263: 814]. CGQRETPEGAEAKPWYC (SEQ ID NO:3) may be used in combination with a pulmonary surfactant either in linear or in circularized form.

Therefore, in accordance with present invention, the term "peptide" refers to a polymer of amino acids (aa) derived from the trypanolytic TNF domain having lectin-like affinity as described by Lucas et al. [Lucas R et al. (1994) Science 263: 814]. Moreover, the latter term relates to a polymer of 7, 8, 9, 10, 11, 12, 13, 14, 15, 16 or 17 contiguous aa derived from the region of human TNF-α from Ser100 to Glul116 or from the region of mouse TNF-α from Ser99 to Glul115.

The term "peptide" more specifically relates to a peptide comprising the hexamer TPEGAE of the latter TNF regions or any peptide comprising the corresponding amino acids T, E and E of the latter hexamer which were shown to be three critical amino acids by Lucas et al. [Lucas R et al. (1994) Science 263: 814].

Furthermore, present invention refers to pharmaceutical compositions comprising a pulmonary surfactant and a TNF-derived peptide as described above wherein said peptide is circularized. More specifically, the present invention refers to pharmaceutical compositions comprising a pulmonary surfactant and a TNF-derived peptide, wherein said peptide is circularized by replacing the NH2- and COOH-terminal amino acids by cysteine so that a disulfide bridge is formed between the latter cysteines. In this regard, the present invention concerns a pharmaceutical composition comprising a pulmonary surfactant and a TNF-derived peptide, wherein said the circularized peptide is CGQRETPEGAEAKPWYC (SEQ ID NO:3) as described by Lucas et al. [Lucas R et al. (1994) Science 263: 814].

It should be clear that present invention relates to any peptide derived from the latter TNF regions and does not exclude post-translational modifications of the peptides such as glycosylation, acetylation, phosphorylation, modifications with fatty acids and the like. Included within present invention are, for example, peptides containing one or more analogues of an aa (including unnatural aa's), peptides with substituted linkages, mutated versions or natural sequence variations of the peptides, peptides containing disulfide bonds between cysteine residues, as well as other modifications known in the art.

The peptides of the present invention can be prepared by any method known in the art such as classical chemical synthesis, as described by *Houben-Weyl [Houben-Weyl Methods of Organic Chemistry. Synthesis of Peptides and Peptidomimetics* (M. Goodman, A. Felix, L. Moroder, C. Toniolo, Eds), Georg Thieme Verlag, Stuttgart and New York, 2003] or by means of recombinant DNA techniques as described in Molecular Cloning [Molecular Cloning: A Laboratory Manual, by Joseph Sambrook and David Russell, Third Edition, Cold Spring Harbor Laboratory, 2001, 3 Volumes] and, more specifically, by Lucas et al. [Lucas R et al. (1994) Science 263: 814].

The term "edema" (or oedema) relates to any abnormal excess accumulation of (serous) fluid in connective tissue or in a serous cavity. In particular, the latter term relates to "pulmonary edema".

According to this invention, pulmonary edema is characterized by a shift of liquid from the pulmonary vessels to the interstitial spaces and the alveolar lumen (interstitial or alveolar edema). Based on their genesis, edema may be divided in hydrostatic and permeability edema, with hydrostatic edema having cardiogenic origin (high blood pressure) and permeability edema occurring after alterations which lead to higher permeability of the endothelial and/or epithelial cell layer at the airway/vessel interface in the lung. Accordingly, the phrase "treating pulmonary edema" refers to any intervention, therapy, condition, or alteration that reverses partially or fully the above mentioned mechanisms of liquid-transfer from the pulmonary vessels to the interstitial spaces and the alveolar lumen and reverses both hydrostatic and permeability edema.

The phrase "combined use" (or "combination") embraces the administration of a pulmonary surfactant and a peptide of present invention as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). "Combined use" generally is not intended to encompass the administration of two of these therapeutic agents as part of separate monotherapy regimens that incidentally and arbitrarily result in the combinations of the present invention.

"Combined use" or "combination" within the meaning of the present invention is to be understood as meaning that the individual components of the combination can be administered simultaneously (in the form of a combination medicament—"fixed combination") or more or less simultaneously, respectively in succession (from separate pack units—"free combination"; directly in succession or else alternatively at a relatively large time interval) in a manner which is known per se and customary. As an example, one therapeutic agent could be taken in the morning and one later in the day. Or in another scenario, one therapeutic agent could be taken once daily and the other twice weekly. It is understood, that if individual components are administered directly in succession, the delay in administering the second component should not be such as to lose the beneficial therapeutic effect of the combination.

It is to be understood that present invention covers all combinations of particular and preferred aspects of the invention described herein. Thus, present invention clearly refers to all compounds or preparations mentioned herein as examples of a pulmonary surfactant and to all compounds mentioned herein as a peptide and to all possible consequential combinations. In particular, combinations which may be mentioned as preferred examples of a combination of a pulmonary surfactant and a peptide are

- a peptide characterized by an amino acid sequence comprising the hexamer $TX_1EX_2X_3E$, wherein $X_1$, $X_2$ and $X_3$ can be any natural or unnatural amino acid, and LUSUPULTIDE,
- a peptide characterized by an amino acid sequence comprising the hexamer TPEGAE (SEQ ID NO:1) and LUSUPULTIDE,
- a peptide comprising the amino acids QRETPEGAEAKPWY (SEQ ID NO:2) and LUSUPULTIDE,
- a peptide comprising the amino acids CQRETPEGAEAKPWYC (SEQ ID NO:3) and LUSUPULTIDE,
- a circularized peptide comprising the amino acids CQRETPEGAEAKPWYC (SEQ ID NO:3) and LUSUPULTIDE,
- a peptide characterized by an amino acid sequence comprising the hexamer $TX_1EX_2X_3E$, wherein $X_1$,$X_2$ and $X_3$ can be any natural or unnatural amino acid, and PORACTANT ALFA,
- a peptide characterized by an amino acid sequence comprising the hexamer TPEGAE (SEQ ID NO:1) and PORACTANT ALFA,
- a peptide comprising the amino acids QRETPEGAEAKPWY (SEQ ID NO:2) and PORACTANT ALFA,
- a peptide comprising the amino acids CQRETPEGAEAKPWYC (SEQ ID NO:3) and PORACTANT ALFA, a circularized peptide comprising the amino acids CQRETPEGAEAKPWYC (SEQ ID NO:3) and PORACTANT ALFA, a peptide characterized by an amino acid sequence comprising the hexamer $TX_1EX_2X_3E$, wherein $X_1$, $X_2$ and $X_3$ can be any natural or unnatural amino acid, and BERACTANT, a peptide characterized by an amino add sequence comprising the hexamer TPEGAE (SEQ ID NO:1) and BERACTANT, a peptide comprising the amino adds QRETPEGAEAKPWY (SEQ ID NO:2) and BERACTANT, a peptide comprising the amino acids CQRETPEGAEAKPWYC (SEQ ID NO:3) and BERACTANT, a circularized peptide comprising the amino acids CQRETPEGAEAKPWYC (SEQ ID NO:3) and BERACTANT, a peptide characterized by an amino acid sequence comprising the hexamer $TX_1EX_2X_3E$, wherein $X_1$, $X_2$ and $X_3$ can be any natural or unnatural amino acid, and BOVACTANT, a peptide characterized by an amino add sequence comprising the hexamer TPEGAE (SEQ ID NO:1) and BOVACTANT, a peptide comprising the amino adds QRETPEGAEAKPWY (SEQ ID NO:2) and BOVACTANT, a peptide comprising the amino acids CQRETPEGAEAKPWYC (SEQ ID NO:3) and BOVACTANT, a circularized peptide comprising the amino acids CQRETPEGAEAKPWYC (SEQ ID NO:3) and BOVACTANT, a peptide characterized by an amino acid sequence comprising the hexamer $TX_1EX_2X_3E$, wherein $X_1$, $X_2$ and $X_3$ can be any natural or unnatural amino acid, and COLFOSCERIL PALMITATE, a peptide characterized by an amino add sequence comprising the hexamer TPEGAE (SEQ ID NO:1) and COLFOSCERIL PALMITATE, a peptide comprising the amino acids QRETPEGAEAKPWY (SEQ ID NO:2) and COLFOSCERIL PALMITATE, a peptide comprising the amino adds CQRETPEGAEAKPWYC (SEQ ID NO:3) and COLFOSCERIL PALMITATE, a circularized peptide comprising the amino acids CQRETPEGAEAKPWYC (SEQ ID NO:3) and COLFOSCERIL PALMITATE, a peptide characterized by an amino acid sequence comprising the hexamer $TX_1EX_2X_3E$, wherein $X_1$, $X_2$ and $X_3$ can be any natural or unnatural amino add, and SURFACTANT-TA, a peptide characterized by an amino add sequence comprising the hexamer TPEGAE (SEQ ID NO:1) and SURFACTANT-TA, a peptide comprising the amino adds QRETPEGAEAKPWY (SEQ ID NO:2) and SURFACTANT-TA, a peptide comprising the amino acids CQRETPEGAEAKPWYC (SEQ ID NO:3) and SURFACTANT-TA, a circularized peptide comprising the amino acids CQRETPEGAEAKPWYC (SEQ ID NO:3) and SURFACTANT-TA, a peptide characterized by an amino acid sequence comprising the hexamer $TX_1EX_2X_3E$, wherein $X_1$, $X_2$ and $X_3$ can be any natural or unnatural amino acid, and CALFACTANT, a peptide characterized by an amino add sequence comprising the hexamer TPEGAE (SEQ ID NO:1) and CALFACTANT, a peptide comprising the amino adds QRETPEGAEAKPWY (SEQ ID NO:2) and CALFACTANT, a peptide comprising the amino acids CQRETPEGAEAKPWYC (SEQ ID NO:3) and CALFACTANT, a circularized peptide comprising the amino acids CQRETPEGAEAKPWYC (SEQ ID NO:3) and CALFACTANT, a peptide characterized by an amino acid sequence comprising the hexamer $TX_1EX_2X_3E$, wherein $X_1$, $X_2$ and $X_3$ can be any natural or unnatural amino acid, and PUMACTANT, a peptide characterized by an amino acid sequence comprising the hexamer TPEGAE (SEQ ID NO:1) and PUMACTANT, a peptide comprising the amino adds QRETPEGAEAKPWY (SEQ ID NO:2) and PUMACTANT, a peptide comprising the amino acids CQRETPEGAEAKPWYC (SEQ ID NO:3) and PUMACTANT, a circularized peptide comprising the amino acids CQRETPEGAEAKPWYC (SEQ ID NO:3) and PUMACTANT a peptide characterized by an amino acid sequence comprising the hexamer $T_1EX_2X_3E$, wherein $X_1$, $X_2$ and $X_3$ can be any natural or unnatural amino acid, and BLES, a peptide characterized by an amino acid sequence comprising the hexamer TPEGAE (SEQ ID NO:1) and BLES, a peptide comprising the amino adds QRETPEGAEAKPWY (SEQ ID NO:2) and BLES, a peptide comprising the amino acids CQRETPEGAEAKPWYC (SEQ ID NO:3) and BLES, a circularized peptide comprising the amino adds CQRETPEGAEAKPWYC (SEQ ID NO:3) and BLES, a peptide characterized by an amino acid sequence comprising the hexamer $TX_1EX_2X_3E$, wherein $X_1$, $X_2$ and $X_3$ can be any natural or unnatural amino acid, and SINAPULTIDE, a peptide characterized by an amino add sequence comprising the hexamer TPEGAE (SEQ ID NO:1) and SINAPULTIDE, a peptide comprising the amino adds QRETPEGAEAKPWY (SEQ ID NO:2) and SINAPULTIDE, a peptide comprising the amino acids CQRETPEGAEAKPWYC (SEQ ID NO:3) and SINAPULTIDE, and a circularized peptide comprising the amino acids CQRETPEGAEAKPWYC (SEQ ID NO:3) and SINAPULTIDE.

Particularly preferred is the combined use of a peptide characterized by an amino acid sequence comprising the hexamer $TX_1EX_2X_3E$, wherein $X_1$, $X_2$ and $X_3$ can be any natural or unnatural amino acid, and LUSUPULTIDE, a peptide characterized by an amino acid sequence comprising the hexamer TPEGAE (SEQ ID NO:1) and LUSUPULTIDE, a peptide comprising the amino adds QRETPEGAEAKPWY (SEQ ID NO:2) and LUSUPULTIDE, a peptide comprising the amino acids CQRETPEGAEAKPWYC (SEQ ID NO:3) and LUSUPULTIDE, or a circularized peptide comprising the amino acids CQRETPEGAEAKPWYC (SEQ ID NO:3) and LUSUPULTIDE.

More or less simultaneous administration of each therapeutic agent can be effected by, for example, intratracheal or intrabronchial administration to the subject in need thereof either as an instillation of the dissolved therapeutic agents, or as an aerosolised liquid or as a dry powder having a fixed ratio of each therapeutic agent.

Administration of each therapeutic agent in succession, close in time or remote in time, can be effected by any appropriate route, including, but not limited to, intratracheal or intrabronchial instillation or by inhalation. The therapeutic agents can be administered by the same route or by different routes. For example, a pulmonary surfactant may be administered by intratracheal or intrabroncheal instillation while the peptide may be administered by inhalation. The sequence in which the therapeutic agents are administered is not narrowly critical.

The most preferred route of administration of a pulmonary surfactant is the intratracheal or intrabronchial route by instillation in liquid form or as aerosolised liquid or as dry powder. It is also preferred that the pulmonary surfactant is administered in form of an aerosolised liquid or a dry powder by inhalation. Dry powder formulations of pulmonary surfactants are preferably prepared by the spray drying process as described in WO 9726863.

The most preferred route of administration of a peptide of present invention is the intratracheal or intrabronchial route by instillation in liquid form or as aerosolised solution or as dry powder.

In case of intratracheal or intrabronchial administration of a pulmonary surfactant preparation, it has proven advantageous to administer suspensions or solutions of the preparations according to the invention which contain 10 to 100 mg of phospholipids per ml of suspension. Preferably, the preparations according to the invention are administered per application in such an amount that the amount of phospholipids is between 10 and 400 mg per kilogram of body weight. As a rule, administration is carried out 1 to 3 times daily over a period of 1 to 7 days. A process is preferred in which the pulmonary surfactant suspension or solution employed contains 0.5 to 2.0 mg of rSP-C (FF/I) per ml of solvent. Particular mention may be made of a process in which the pulmonary surfactant solution employed contains 0.75 to 1.5 mg of rSP-C (FF/I) per ml of solvent.

Generally, a peptide of present invention is administered at a dose between 1 microg/kg and 10 mg/kg, more preferably between 10 microg/kg and 5 mg/kg, most preferably between 0.1 and 2 mg/kg. In case of intratracheal or intrabronchial instillation a peptide of present invention is administered at a dose of 1-10 mg/ml/kg body weight, particularly preferred at a dose of 1-2 mg/ml/kg body weight. In case the peptide of present invention is administered as an aerosol or by intratracheal nebulization, the peptide is administered in a dose between 1-10 mg/ml/kg body weight, particularly preferred at a dose of 1-2 mg/ml/kg body weight.

In spite of this, if appropriate it may sometimes be necessary to depart from the amounts mentioned, mainly depending on the body weight or the type of administration route, on individual behavior towards the medicament, the manner of its formulation and the time or interval at which administration takes place. Thus in some cases it may be sufficient to manage with less than the abovementioned minimum amount, while in other cases the upper limit mentioned has to be exceeded. In the case of the administration of relatively large amounts, it may be advisable to divide these into several individual doses over the course of the day.

In case of fixed pharmaceutical compositions, which are intended for intratracheal or intrabronchial instillation or for inhalation, the therapeutic agent(s) are formulated to give medicaments according to processes known per se and familiar to the person skilled in the art. The therapeutic agents are employed as a medicament, preferably in combination with a salt, such as NaCl, preferably in 0,9% NACl, the therapeutic agent content advantageously being between 0.1 and 95% by weight of total volume.

In case of free pharmaceutical compositions, which are intended for intratracheal or intrabronchial instillation, each therapeutic agent is formulated to give a medicament according to processes known per se and familiar to the person skilled in the art. Each therapeutic agent is employed as a medicament, preferably in combination with a salt, such as NaCl, preferably in 0,9% NACl, the therapeutic agent content advantageously being between 0.1 and 95% by weight of total volume.

The therapeutic agent(s) of the present invention can be administered by a variety of methods known in the art, although for many therapeutic applications, the preferred route of administration is a fixed combination of a pulmonary surfactant and a peptide of present invention whereby the combination product is administered as a dry powder or as an aerosol by inhalation or by intratracheal or intrabronchial instillation of a liquid. For some therapeutic application it may be preferable to administer the pulmonary surfactant and the peptide of present invention as a free combination, whereby the preferred route of administration is the intrabronchial instillation of single liquid formulations.

The therapeutic agent(s) are dosed in an order of magnitude customary for the individual dose. It is more likely possible that the individual actions of the therapeutic agents are mutually positively influenced and reinforced and thus the respective doses on the combined administration of the therapeutic agent(s) may be reduced compared with the norm.

Utility

Pharmaceutical compositions of present inventions comprising a combination of a pulmonary surfactant and a peptide have beneficial effects compared to pharmaceutical compositions comprising solely one of these active ingredients.

Firstly, it has surprisingly been found that an unexpected therapeutic benefit, particularly a synergistic benefit, can be seen by administering a combination of a pulmonary surfactant and a peptide of present invention to a patient suffering from ARDS, IRDS, ALI or lung edema. For instance, it is possible by using a combination of a pulmonary surfactant and a peptide of present invention to superiorly ameliorate oxygenation in a patient in need thereof suffering from ARDS, IRDS, ALI or lung edema. This synergistic effect of the combination of a pulmonary surfactant and a peptide of present invention has been shown by in vivo studies as outlined in Example 5 and FIG. 1.

Secondly, there is provided as a result of the improved oxygenation a significantly improvement of patients body performance—compared to the use of a pulmonary surfactant alone.

Thirdly, because of the above-mentioned synergistic effect of a combination of present invention, the amount of the pulmonary surfactant may be significantly reduced when used in a combination with a peptide of present invention. As pulmonary surfactant are comparatively costly and peptides of present invention may be produced cost-saving by chemical synthesis, the cost of a treatment of a patient suffering from ARDS, IRDS, ALI or lung edema may be significantly reduced.

Fourthly, when using a combination product of present invention for the treatment of a patient suffering from ARDS, IRDS, ALI or lung edema, the frequency of ungratefulness related to the application of a pulmonary surfactant, for example, by instillation may also be reduced compared to the use of a pulmonary surfactant alone.

Fifthly, it has been found that the use of a combination of a pulmonary surfactant and a peptide of present invention significantly reduces the time patients with ARDS or IRDS have to be ventilated, and thus, it is possible by the administration of a combination of a pulmonary surfactant and a peptide of present invention to avoid side effects of ventilation, for example the risk of a nosocomial infection or pneumonia for the patients can be lowered compared to the use of a pulmonary surfactant alone.

Finally, it has been proven advantageous to prescribe combinations of single active ingredients in the form of a "patient pack" containing the whole course of treatment in a single package. This procedure is also applicable for the pharmaceutical compositions of present invention. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions and, therefore, lead generally to more successful treatment. It will be understood that the administration of a combination of present invention by means of a single patient pack, or patent packs of each component compound, and containing a package insert instructing the patient to the correct use of the invention is a desirable additional feature of the invention leading to an increased compliance of the patient compared to the administration of each single component.

DESCRIPTION OF DIAGRAMS

FIG. 1: Influence of combined administration of the circularized peptide CGQRETPEGAEAKPWYC (SEQ ID NO:3) (=TIP) and LUSUPULTIDE on arterial blood oxygenation Male Wistar rats were prepared as disclosed in Example 5. NaCl 0.9% (open circles), LUSUPULTIDE 12.5 mgPL/kg (filled squares), the circularized peptide CGQRETPEGAEAKPWYC (SEQ ID NO:3) (=TIP) 500 μg/animal (stars), or LUSUPULTIDE 12.5 mgPL/kg in combination with TIP 500 μg/animal (open squares) was administered intratracheally (administration volume 1.2 mL, solvent NaCl 0.9%). Arterial blood oxygenation ($PaO_2$) was determined every 30 min up to 150 min after drug administration (t=210 min). Administration of NaCl and TIP alone had no influence on oxygenation, but LUSUPULTIDE 12.5 mgPL/kg improved oxygenation to about 200-300 mmHg. Combination of both drugs, LUSUPULTIDE 12.5 mgPL/kg containing TIP 500 μg/animal, showed a significant, synergistic effect in restoring the oxygenation. Data are shown as mean ±SEM.*$p<0.05$, **$p<0.01$ versus LUSUPULTIDE 12.5 mgPL/kg

EXAMPLES

According to this invention, the term "TIP" as used in the following examples refers to a circularized peptide of present invention having the amino acid sequence of CGQRETPEGAEAKPWYC (SEQ ID NO:3).

Example 1

Fixed Combination LUSUPULTIDE+TIP for Intrabronchial Instillation 9.8 g of 1,2-dipalmitoyl-3-sn-phosphatidylcholine, 4.2 g of 1-palmitoyl-2-oleoyl-3-sn-phosphatidylglycerolammonium, 0.7 g of palmitic acid, 0.36 g of calcium chloride and 0.28 g of r-SP-C (FF/I) are dissolved in 820 ml of 2-propanol/water (90:10) and spray-dried in a Buchi B 191 laboratory spray-dryer. Spray conditions: drying gas nitrogen, inlet temperature 110° C., outlet temperature 59-61° C. A fine powder is obtained which can be micronized. 180 mg TIP is dissolved in 180 mL 0.9% sodium chloride. The 15.34 g of the surfactant composition are added to this solution and suspended. For a single application in humans 1 ml/kg body weight of this suspension can be instilled intrabronchially guided by a bronchoscope.

Example 2

Fixed Combination LUSUPULTIDE+TIP for Intratracheal Nebulization 9.8 g of 1,2-dipalmitoyl-3-sn-phosphatidylcholine, 4.2 g of 1-palmitoyl-2-oleoyl-3-sn-phosphatidylglycerolammonium, 0.7 g of palmitic acid, 0.36 g of calcium chloride and 0.28 g of r-SP-C (FF/I) are spray-dried as described in Example 1. 360 mg TIP is dissolved in 180 mL 0.9% sodium chloride. The 15.34 g of the surfactant composition are added to this solution and suspended. For a single application in humans 1 ml/kg body weight of this suspension can be nebulized by an Aeroneb Pro aerosol generator (Aerogen Inc., Sterlin Court, Calif.).

Example 3

Free Combination of BERACTANT for Intratracheal Instillation+TIP for Aerosol Administration For a single application in humans commercially available BERACTANT (Survanta®) is administered intratracheally 100 mg/kg as a suspension in 0.9% sodium chloride containing 25 mg phospholipids per mL (consisting of 11.0-15.5 mg/mL disaturated phosphatidycholine, 0.5-1.75 mg/mL triglycerides, 1.4-3.5 mg/mL free fatty acids, and less than 1.0 mg/mL protein). This application is combined with one or several administrations of TIP. Therefore, the TIP 2 mg/mL is dissolved in 0.9% sodium chloride. For a single application in humans 1 ml/kg body weight of this suspension can be nebulized by an Aeroneb Pro aerosol generator (Aerogen Inc., Stierlin Court, Calif.).

Example 4

Free Combination PORACTANT ALPHA for Intratracheal Instillation+TIP-peptide for Intratracheal Instillation For a single application in humans commercially available PORACTANT ALPHA (Curosurf.RTM.) is administered intratracheally 100-200 mg/kg. Composition per mL of suspension: phospholipid fraction from porcine lung 80 mg/mL, equivalent to about 74 mg/mL of total phospholipids and 0.9 mg/mL of low molecular weight hydrophobic proteins. This application is combined with one or several timed intratracheal administrations of 1 mg/kg TIP dissolved in 1 mg/ml 0.9% sodium chloride.

Example 5

Influence of Combined Administration of a Circularized Peptide Comprising the Amino Acid Sequence CGQRETPEGAEAKPWYC (SEQ ID NO:3) and LUSUPULTIDE on Arterial Blood Oxygenation after Repeated Saline Lung Lavage in Rats Male Wistar rats (230-280 g) were anaesthetized, catheterized to withdraw arterial blood, and ventilated with pure oxygen (=>$PaO_2$~500-550 mmHg). 30 min later lungs were ravaged 5-9 times with NaCl 0.9% (=>$PaO_2$~50-100 mmHg). After 60 min NaCl 0.9%, LUSUPULTIDE 12.5 mgPL/kg, TIP (500 μg/animal), or LUSUPULTIDE (12.5 mgPL/kg) in combination with TIP (500 μg/animal) was administered intratracheally (administration volume 1.2 mL, solvent NaCl 0.9%). Arterial blood oxygenation ($PaO_2$) was determined every 30 min up to 150 min after drug administration (t=210 min).

The invention claimed is:

1. A pharmaceutical composition comprising:

a therapeutically effective amount of a pulmonary surfactant selected from the group consisting of CUROSURF®, SURVANTA®, ALVEOFACT®, SURFACTEN@, INFASURF®, BLES®, SINAPULTIDE® and a pulmonary surfactant comprising phospholipids and pulmonary surfactant protein, the pulmonary surfactant protein being selected from the group consisting of Surfactant Protein-B (SP-B), Surfactant Protein-C (SP-C) and LUSUPULTIDE (rSP-C (FF/I)); a therapeutically effective amount of a peptide consisting of the amino acids according to SEQ ID NO: 2 or the amino acids according to SEQ ID NO: 3 and a pharmaceutically acceptable carrier.

2. The pharmaceutical composition according to claim 1, comprising as a fixed combination:

a therapeutically effective amount of a pulmonary surfactant selected from the group consisting of CUROSURF®, SURVANTA®, ALVEOFACT®, SURFACTEN®, INFASURF®, BLES®, SINAPULTIDE® and a pulmonary surfactant comprising phospholipids and pulmonary surfactant protein, the pulmonary surfactant protein being selected from the group consisting of Surfactant Protein-B (SP-B), Surfactant Protein-C (SP-C) and LUSUPULTIDE (rSP-C (FF/I)); and a therapeutically effective amount of a peptide consisting of the amino acids according to SEQ ID NO: 2 or the amino acids according to SEQ ID NO: 3.

3. The pharmaceutical composition according to claim 2, which is a powder formulation.

4. The pharmaceutical composition according to claim 2, which is a liquid formulation.

5. The pharmaceutical composition according to claim 2, which is a fixed pharmaceutical composition for intratracheal or intrabronchial instillation.

6. The pharmaceutical composition according to claim 2, which is a fixed pharmaceutical composition for inhalation.

7. The pharmaceutical composition according to claim 1, comprising as a free combination:

a therapeutically effective amount of a pulmonary surfactant selected from the group consisting of CUROSURF®, SURVANTA®, ALVEOFACT®, SURFACTEN®, INFASURF®, BLES®, SINAPULTIDE® and a pulmonary surfactant comprising phospholipids and pulmonary surfactant protein, the pulmonary surfactant protein being selected from the group consisting of Surfactant Protein-B (SP-B), Surfactant Protein-C (SP-C) and LUSUPULTIDE (rSP-C (FF/I)); and a therapeutically effective amount of a peptide consisting of the amino acids according to SEQ ID NO: 2 or the amino acids according to SEQ ID NO: 3.

8. The pharmaceutical composition according to claim 7, wherein the pulmonary surfactant and the peptide are in a liquid form.

9. The pharmaceutical composition according to claim 7, wherein the pulmonary surfactant and the peptide are in a powder form.

10. The pharmaceutical composition according to claim 7, which is a free pharmaceutical composition for intratracheal or intrabronchial instillation.

11. The pharmaceutical composition according to claim 7, which is a free pharmaceutical composition for inhalation.

12. The pharmaceutical composition according to claim 1, wherein the peptide consists of the amino acids according to SEQ ID NO: 2.

13. The pharmaceutical composition according to claim 1, wherein the peptide consists of the amino acids according to SEQ ID NO: 3.

14. The pharmaceutical composition according to claim 1, wherein the peptide is synthetic.

15. The pharmaceutical composition according to claim 1, wherein the peptide is circularized.

16. The pharmaceutical composition according to claim 1, wherein the pulmonary surfactant is selected from the group consisting of CUROSURF®, SURVANTA®, ALVEOFACT®, SURFACTEN®, INFASURF®, SINAPULTIDE® and a pulmonary surfactant comprising phospholipids and pulmonary surfactant protein, the pulmonary surfactant protein being selected from the group consisting of SP-B, SP-C and rSP-C (FF/I).

17. The pharmaceutical composition according to claim 1, wherein the pulmonary surfactant comprises phospholipids and rSP-C (FF/I).

18. The pharmaceutical composition according to claim 1, wherein the pulmonary surfactant comprises 80 to 95% by weight of phospholipids, 0.5 to 3.0% by weight of pulmonary surfactant proteins, 3 to 15% by weight of fatty acid, and 0 to 3% by weight of calcium chloride.

19. The pharmaceutical composition according to claim 1, wherein the pulmonary surfactant is selected from the group consisting of CUROSURF®, SURVANTA®, ALVEOFACT®, SURFACTEN®, and INFASURF®.

* * * * *

UNITED STATES PATENT AND TRADEMARK OFFICE

CERTIFICATE OF CORRECTION

PATENT NO. : 8,236,750 B2
APPLICATION NO. : 11/658727
DATED : August 7, 2012
INVENTOR(S) : Klaus P. Schaefer, Stefan-Lutz Wollin and Ingeborg Muehldorfer It is certified that error appears in the above-identified patent and that said Letters Patent is hereby corrected as shown below:

Column 15, Claim 1, Lines 45-46
Please delete "SURFACTEN@"
and replace with --SURFACTEN®--

Signed and Sealed this
Twenty-third Day of October, 2012

David J. Kappos
*Director of the United States Patent and Trademark Office*

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial
<220> FEATURE:
<223> OTHER INFORMATION: TNF-derived peptide

<400> SEQUENCE: 1

Thr Pro Glu Gly Ala Glu
1               5


<210> SEQ ID NO 2
<211> LENGTH: 14
<212> TYPE: PRT
<213> ORGANISM: Artificial
<220> FEATURE:
<223> OTHER INFORMATION: TNF-derived peptide

<400> SEQUENCE: 2

Gln Arg Glu Thr Pro Glu Gly Ala Glu Ala Lys Pro Trp Tyr
1               5                   10


<210> SEQ ID NO 3
<211> LENGTH: 17
<212> TYPE: PRT
<213> ORGANISM: Artificial
<220> FEATURE:
<223> OTHER INFORMATION: TNF-derived peptide

<400> SEQUENCE: 3

Cys Gly Gln Arg Glu Thr Pro Glu Gly Ala Glu Ala Lys Pro Trp Tyr
1               5                   10                  15

Cys
```